United States Patent [19]
Bristow et al.

[11] 4,104,625
[45] Aug. 1, 1978

[54] APPARATUS FOR PROVIDING FACIAL IMAGE ANIMATION

[75] Inventors: Stephen D. Bristow, Los Altos Hills; Nolan K. Bushnell, Woodside, both of Calif.

[73] Assignee: Atari, Inc., Sunnyvale, Calif.

[21] Appl. No.: 758,714

[22] Filed: Jan. 12, 1977

[51] Int. Cl.$^2$ .......................................... G06K 15/18
[52] U.S. Cl. ................ 340/324 R; 179/1 SP; 352/50; 352/87; 353/30; 353/48
[58] Field of Search ....... 340/324 R, 324 A, 324 AD, 340/325; 178/15; 352/15, 50, 54, 47, 87; 179/1 SP; 353/30, 48

[56] References Cited
U.S. PATENT DOCUMENTS

| | | | |
|---|---|---|---|
| 2,501,958 | 3/1950 | O'Brien | 352/54 X |
| 3,182,574 | 5/1965 | Fleisher et al. | 178/15 X |
| 3,531,193 | 9/1970 | Diehl | 352/87 |
| 3,573,785 | 4/1971 | Miller et al. | 340/324 R |
| 3,662,374 | 5/1972 | Harrison et al. | 340/324 A |
| 3,797,012 | 3/1974 | Gibbs et al. | 340/148 X |

Primary Examiner—David L. Trafton
Attorney, Agent, or Firm—Flehr, Hohbach, Test, Albritton & Herbert

[57] ABSTRACT

An image animation apparatus includes a rotating disk having film negatives mounted around its periphery each film negative having a different facial expression on it. By use of an associated microprocessor which responds to certain control inputs the sequence of facial expressions can be selected by activating a flash tube at the proper time to project the image on the face of a featureless mannequin to cause the sequence of facial expressions to correspond to spoken phonemes which are synchronized with the facial expressions. Alternatively, instead of a rotating disk a matrix of optical cells can be selectively flashed. In addition, the image forming film negative associated with each optical cell can either contain a complete facial expression or a portion such as the eyes, mouth or eyebrows with the simultaneous activation of, for example, three cells producing a complete facial expression.

7 Claims, 9 Drawing Figures

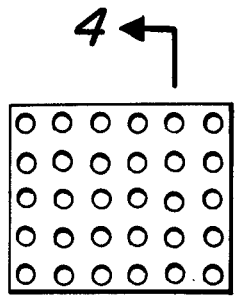
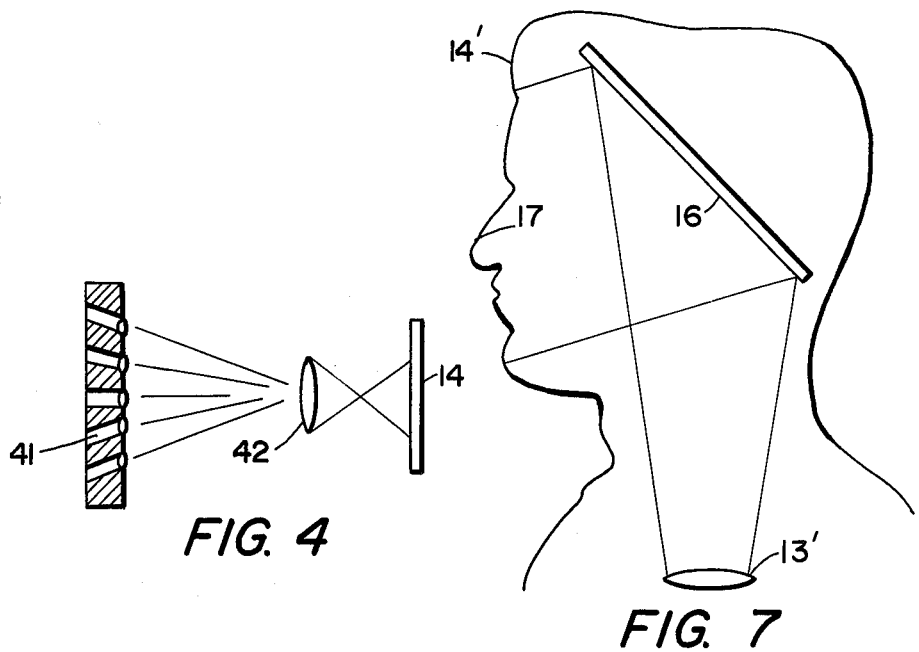
FIG. 3
FIG. 4
FIG. 7
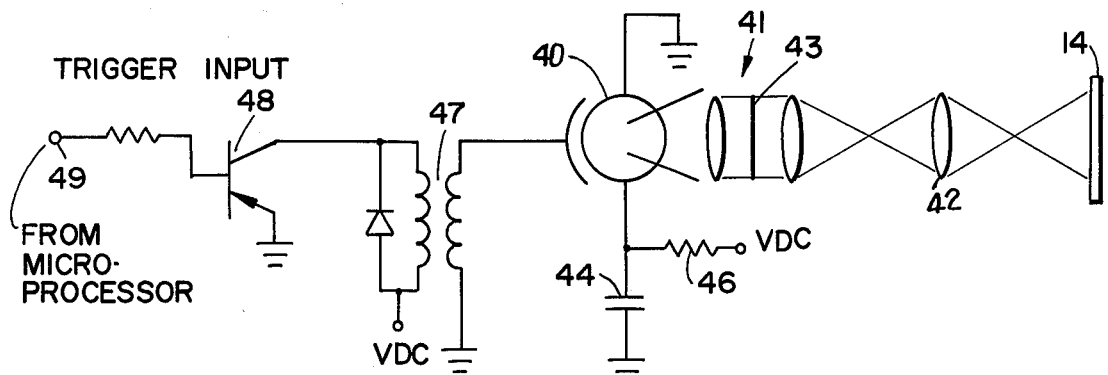
FIG. 5
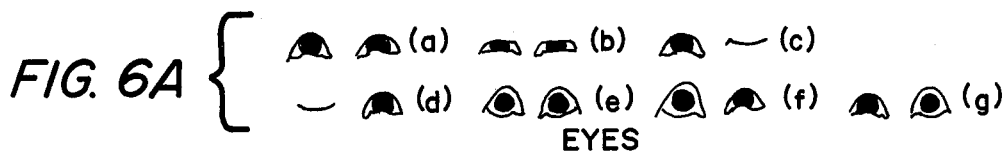
FIG. 6A  EYES
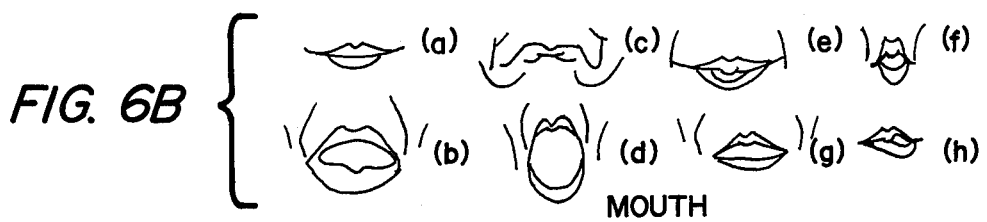
FIG. 6B  MOUTH
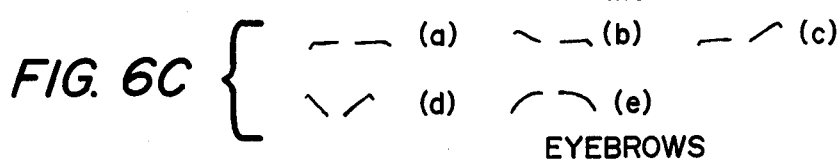
FIG. 6C  EYEBROWS

APPARATUS FOR PROVIDING FACIAL IMAGE ANIMATION

BACKGROUND OF THE INVENTION

The present invention is directed to apparatus for providing facial image animation and more specifically for animating the face of a featureless mannequin used in conjunction with a video game.

To provide image animation, film projection on a featureless face has been used; e.g., see the "Haunted House" at the Disneyland theme type amusement park in Anaheim, California. Film strips have also been used for display of alpha-numeric characters as shown in U.S. Pat. No. 3,727,214 with Ronald G. Wayne as inventor. Such film techniques are subject to excessive wear. Also the sequence of expressions is fixed.

OBJECTS AND SUMMARY OF THE INVENTION

It is, therefore, a general object of the present invention to provide improved apparatus for providing facial image animation.

It is another object to provide animation apparatus which is not subject to excessive wear and which has a capability of producing several different expression sequences.

In accordance with the above objects there is provided apparatus for providing facial image animation with a plurality of image forming units each with at least a portion of a facial expression corresponding to a spoken phoneme. Means are provided for visually displaying images received from said forming units. Means selectively activate a plurality of image forming units in any of a plurality of different facial expression sequences.

BRIEF DESCRIPTION OF THE DRAWINGS

FIG. 3 is a front view of another embodiment of the invention;

FIG. 4 is a cross-sectional view taken along line 4—4 of FIG. 3 and also shows associated optics;

FIG. 5 is an electro-optical detailed schematic of the embodiment of FIGS. 3 and 4;

FIGS. 6A, 6B and 6C are portions of facial expressions used in the embodiment of FIGS. 3, 4 and 5; and FIG. 7 is a simplified cross-sectional side view of the featureless face of a mannequin used in the present invention.

DETAILED DESCRIPTION OF THE PREFERRED EMBODIMENT

Figure 1:
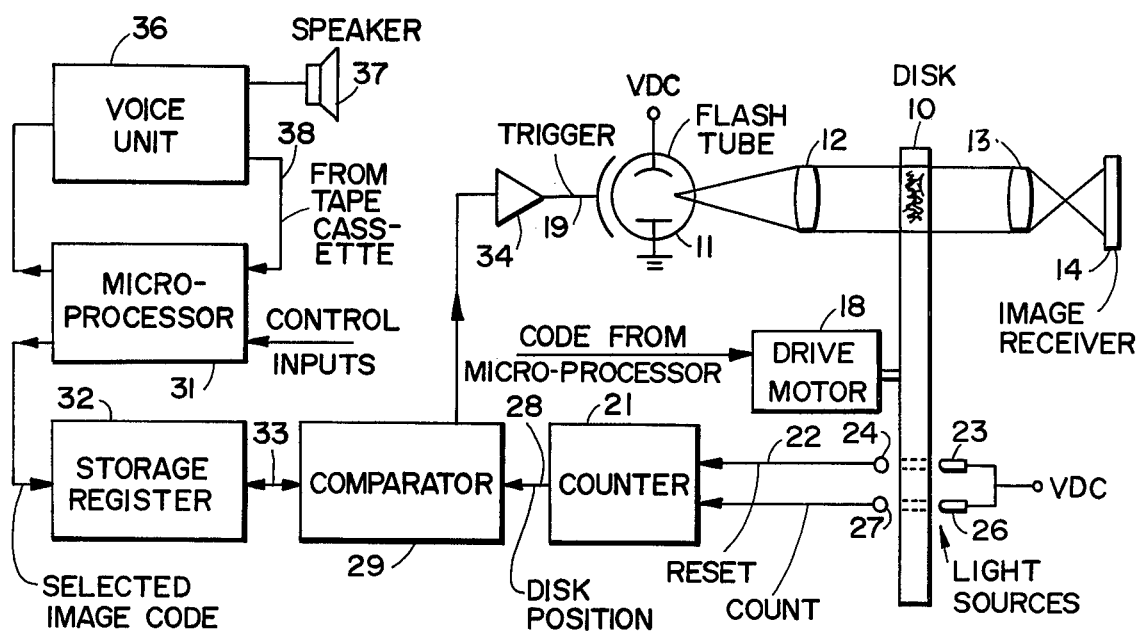
FIG. 1 is a block diagram of one embodiment of the present invention.
Figure 2:
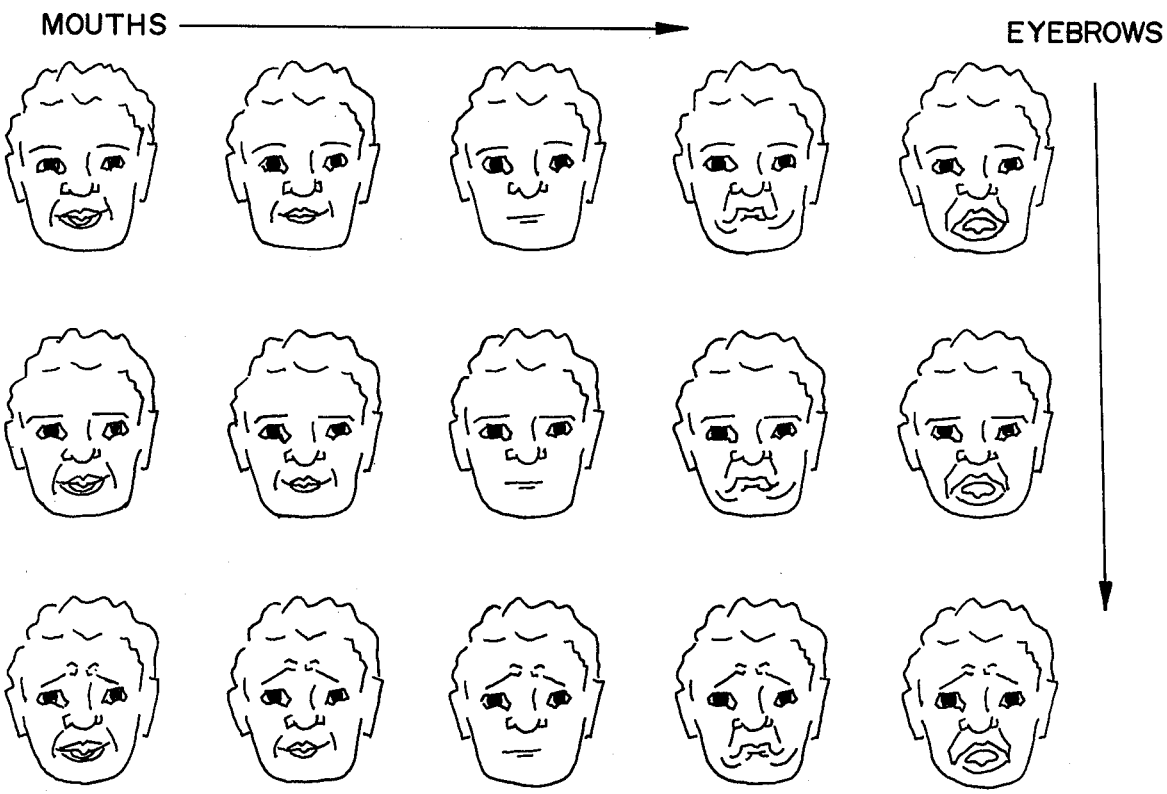
FIG. 2 illustrates a set of faces used in FIG. 1.

Referring now to FIGS. 1 and 2, a rotary disk 10 carries on its periphery several film negatives of facial expressions as illustrated in FIG. 2. When it is illuminated by a flash tube 11 and focused by lenses 12 and 13 onto an image receiver or screen, 15 different facial expressions as shown in FIG. 2 can be produced in any desired sequence. Thus, a specific sequence of facial expressions or perhaps one facial expression can correspond to a spoken phoneme and in fact a total spoken phrase can be facially animated.

FIG. 7 illustrates a typical image receiver 14' which is a mannequin having a featureless face where the output from a lens 13' from the image forming units is reflected off a mirror 16 onto the featureless face.

As illustrated in FIG. 2, variation in mouth expression is changed from left to right and in eyebrow expression or configuration from top to bottom. Thus, the 15 faces of FIG. 2 are actually film negatives placed around the periphery of disk 10 to provide various permutations of facial expressions which as will be discussed below when selected in different sequences can produce any of a plurality of different phoneme sequences. The various picture images shown in FIG. 2 are of course only representative. That is, the number of film negatives is determined by the number of individual movements or the clarity of motion that is desired. Also although in the preferred embodiment the facial expressions of FIG. 2 are typically on film negatives, the expressions could be in the form of holographic data suitable for three dimensional projection.

Referring again to FIG. 1, disk 10 is continuously rotated by a drive motor 18 in the preferred embodiment and an image is produced only when the flash tube 11 is triggered on its line 19. The rotary position of disk 10 and therefore the particular image forming unit or face which is in the lens system 12, 13, is sensed by a counter 21 which has a zero or reset input 22 which is produced by a light source of the light emitting diode type 23 activating a photo-sensor 24. A count input produced by a light source 26 activating photo sensor 27. The reset input could be produced by a single aperture in disk 10 and the count input by a sequence of apertures, one for each film negative of a picture, as illustrated by the dashed lines through the disk 10.

Thus, output 28 of counter 21 represents disk position and is compared by comparator 29 with the desired image determined by microprocessor 31 and storage register 32 on line 33 which is connected to comparator 29. When equality is indicated by comparator 29, trigger line 19 of flash tube 11 is activated through amplifier 34. At the same time, microprocessor 31 activates a voice unit 36 which drives a loudspeaker 37 to produce an appropriate audio sound.

Drive motor 18 instead of being continuously driven can theoretically be driven in an open loop mode stopping at each desired picture position by a daisy wheel drive technique now used in automatic typewriters as, for example, illustrated in U.S. Pat. No. 3,954,163.

One control mode of operation is shown in FIG. 1 where the voice unit 36 contains an audio tape cassette driving the loudspeaker 37 the tape also having a subaudible control track whose signals are communicated to the microprocessor 31 on line 38. The subaudible signals cause the facial expressions to correspond to the set of spoken phoneme which are audibly recorded on the tape cassette and produced by the loudspeaker. Alternatively, microprocessor 31 could have control inputs from a read only memory which contains several different sequences of facial expressions for different external conditions of, for example, the video game with which the present invention is associated. For example, the mannequin could respond in a life-like way to questions, buttons being pressed, etc. In fact, for even more realistic action the microprocessor could select phrases and words or parts of words from a recording device and by decoding techniques convert these to a sequence of facial expressions.

FIGS. 3 through 5 show another embodiment of the invention where as illustrated in FIG. 3 a matrix of 30 optical cells provide different images which may be projected as illustrated in FIGS. 4 and 5 on the image receiver 14. The cell would typically contain a film negative of either a full image of a facial expression of the type as shown in FIG. 2 or alternatively, a portion of a facial expression such as the eyes, mouth or eyebrows shown in FIGS. 6A through 6C. Thus by simultaneous activation of three optical cells a complete facial expression can be formed. The technique of using partial facial expressions allows many more permutations.

FIG. 4 is a cross-section of the optical cell matrix of FIG. 3 and shows the individual cell units 41 directed toward the focusing lens 42. In the detailed schematic of FIG. 5 the cell 41 includes a flash tube 40, for example of the xenon type, a film negative 43 having a portion of a facial expression corresponding to one of those in FIGS. 6A through C and various focusing lens. Flash tube 40 is supplied energy from a storage capacitor 44 which is charged through a resistor 46 by a dc voltage source. Flash tube 40 is triggered through a transformer 47 activated through a transistor 48 having a base triggering input 49 connected to the microprocessor 31.

Variations of the optical cell 41 are, of course, possible and include the use of a mechanical shutter instead of a flash tube. A further modification is replacement of the mechanical shutter with an electronic shutter. Both the shutter embodiments have the advantage that a continuous light source can be used and thus the rise time of a light source does not have to be compensated for. A typical electronic shutter might be a Kerr cell arranged with a pair of polarizers.

Thus, an improved apparatus for producing image animation has been provided.

What is claimed is:

1. Apparatus for providing facial image animation comprising: a plurality of image forming units each with at least a portion of a facial expression corresponding to a spoken phoneme; means for visually displaying images received from said forming units; and means for selectively activating different pluralities of said image forming units in any of a plurality of different orders to provide correspondingly different facial expression sequences.

2. Apparatus as in claim 1 where said image forming units include a rotary disk having image negatives of various facial expressions around its periphery.

3. Apparatus as in claim 2 where said means for selectively activating said image forming units includes means for sensing the rotational position of said disk.

4. Apparatus as in claim 2 where said facial expressions include permutations of different eyebrow and mouth configurations.

5. Apparatus as in claim 1 where said image forming units include a matrix of optical cells.

6. Apparatus as in claim 5 where each of said optical cells includes an image negative of only a portion of a facial expression a group of said cells when simultaneously activated producing a complete facial expression.

7. Apparatus as in claim 1 including audio transducer means for producing audio sounds corresponding to said sequence of facial expressions.

* * * * *